(12) United States Patent
Larsson

(10) Patent No.: US 10,098,754 B2
(45) Date of Patent: Oct. 16, 2018

(54) SPINE CAGE

(71) Applicant: Neo Medical SA, Bourg-en-Lavaux (CH)

(72) Inventor: Jonas Larsson, Bourg-en-Lavaux (CH)

(73) Assignee: Neo Medical S.A., La Villette (CH)

( * ) Notice: Subject to any disclaimer, the term of this patent is extended or adjusted under 35 U.S.C. 154(b) by 0 days.

(21) Appl. No.: 15/306,113

(22) PCT Filed: Apr. 9, 2015

(86) PCT No.: PCT/IB2015/052585
§ 371 (c)(1),
(2) Date: Oct. 24, 2016

(87) PCT Pub. No.: WO2015/162514
PCT Pub. Date: Oct. 29, 2015

(65) Prior Publication Data
US 2017/0042696 A1    Feb. 16, 2017

(30) Foreign Application Priority Data

Apr. 25, 2014    (WO) .................. PCT/IB2014/061000

(51) Int. Cl.
*A61F 2/46*    (2006.01)
*A61F 2/44*    (2006.01)
*A61F 2/30*    (2006.01)

(52) U.S. Cl.
CPC ............ *A61F 2/4455* (2013.01); *A61F 2/447* (2013.01); *A61F 2002/30112* (2013.01); *A61F 2002/30143* (2013.01); *A61F 2002/30146* (2013.01); *A61F 2002/30153* (2013.01); *A61F 2002/30448* (2013.01); *A61F 2002/30904* (2013.01); *A61F 2002/4475* (2013.01)

(58) Field of Classification Search
CPC .............................................. A61F 2/44–2/447
USPC ........................................... 623/17.11–17.16
See application file for complete search history.

(56) References Cited

U.S. PATENT DOCUMENTS

| | | | |
|---|---|---|---|
| 4,834,757 A * | 5/1989 | Brantigan | A61B 17/1604 623/17.11 |
| 5,888,224 A | 3/1999 | Beckers et al. | |
| 6,758,849 B1 * | 7/2004 | Michelson | A61F 2/30744 606/247 |
| 2002/0049499 A1 | 4/2002 | Walkenhorst et al. | |
| 2002/0068976 A1 * | 6/2002 | Jackson | A61F 2/4455 623/17.15 |

(Continued)

FOREIGN PATENT DOCUMENTS

WO    WO 8909035 A1    10/1989

OTHER PUBLICATIONS

International Search Report of the parent application PCT/IB2015/052585 dated Aug. 25, 2015.

(Continued)

*Primary Examiner* — Nicholas Plionis
(74) *Attorney, Agent, or Firm* — Andre Roland S.A.; Nikolaus Schibli

(57) ABSTRACT

A spine cage (1) comprising a pair of opposite functional sides (2,3) and at least another pair of opposite functional sides (4,5), such that the cage can be positioned in at least two different positions providing at least two different configurations.

3 Claims, 1 Drawing Sheet

(56) References Cited

U.S. PATENT DOCUMENTS

| | | | |
|---|---|---|---|
| 2006/0206207 A1* | 9/2006 | Dryer | A61F 2/446 623/17.11 |
| 2006/0293748 A1* | 12/2006 | Alexander | A61F 2/447 623/17.11 |
| 2007/0027544 A1* | 2/2007 | McCord | A61F 2/447 623/17.11 |
| 2011/0015742 A1* | 1/2011 | Hong | A61F 2/447 623/17.11 |
| 2011/0172774 A1 | 7/2011 | Varela | |
| 2012/0089228 A1* | 4/2012 | Poulos | A61F 2/442 623/17.16 |
| 2013/0245763 A1* | 9/2013 | Mauldin | A61F 2/4455 623/17.11 |

OTHER PUBLICATIONS

Written Opinion of International Search Authority of the parent application PCT/IB2015/052585 dated Aug. 25, 2015.
Chinese Office Action issed in the counterrpart China Patent Application No. 201580017803.0 dated Apr. 18, 2018 and English translation thereof.

* cited by examiner

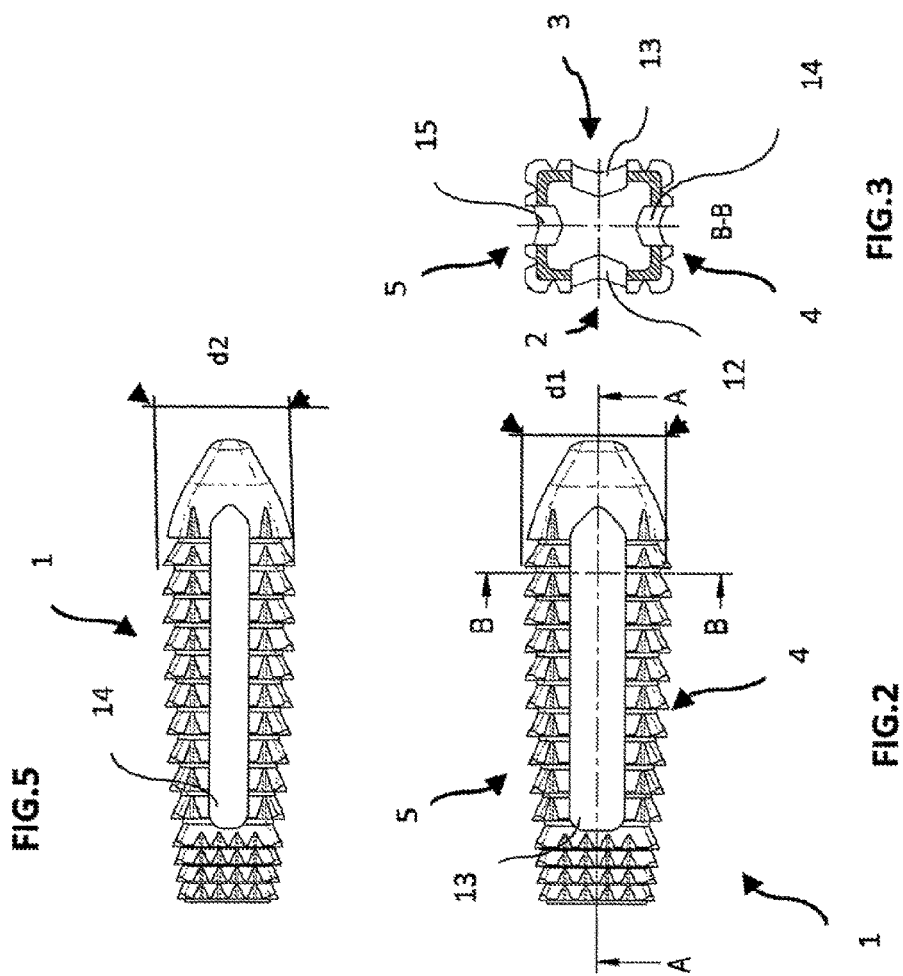

SPINE CAGE

CROSS REFERENCE TO RELATED APPLICATIONS

The present application is a U.S. national stage application of PCT/IB2015/052585 filed on Apr. 9, 2015 designating the United States, and claims foreign priority to International patent application PCT/IB2014/061000 filed on Apr. 25, 2014, the contents of both documents being herewith incorporated by reference in their entirety.

TECHNICAL FIELD

The present invention concerns the field of spine cages, for example to perform a spinal fusion between two or more vertebrae in the spine.

BACKGROUND ART

Documents U.S. Pat. No. 5,888,224, US 20110015742 and US 20110172774 for example show such spine cages.

U.S. Pat. No. 5,888,224 discloses an implant for the intervertebral space which consists of an essentially cuboid body with a device for gripping by a tool.

US 2011/0015742 shows a spine fusion cage comprises a housing, a movable member, a sliding member and a screw. The upper surface of the housing has an opening through which the movable member can move in a vertical direction. The sliding member is provided within the housing and can move in a longitudinal direction of the spine fusion cage. The movable member has an activation surface. In the case that the activation surface is in contact with the sliding member, movement of the sliding member in the longitudinal direction of the spine fusion cage causes the movable member to move up or down. The sliding member is moved by turning the screw such that the movable member can move up or down.

US 2011/0172774 provides an expandable intervertebral implant that is selectively disposed in the intervertebral space and deployed, thereby in-situ distracting, realigning, and/or stabilizing or fusing a portion of the spine of a patient in the treatment of injury, disease, and/or degenerative condition. The expandable intervertebral implant includes a superior member and an inferior member, each of which has a partially or substantially wedge or prismatic shape and a partially or substantially convex or other-shaped surface that is suitable for engaging the substantially concave surfaces of the associated bony superior and inferior intervertebral endplates. Once disposed in the intervertebral space, the expandable intervertebral implant is actuated and deployed, with the superior member and the inferior member moving apart from one another, seating against the associated intervertebral endplates, and distracting, realigning, and/or stabilizing them to a desired degree. The external surface of each of the superior member and the inferior member is provided with a plurality of ridges or other friction structures, providing purchase with the associated intervertebral endplates.

SUMMARY OF THE INVENTION

An aim of the present invention is to improve the known devices and spine cages.

More specifically, an aim of the present invention is to provide a spine cage that is simpler and more efficient that the cages of the prior art.

To this effect, the cage is defined by the features of the claims.

In the present text "functional side" refers to a side of the cage which is in direct contact with a vertebra.

Different embodiments of the invention are described in the following specification.

BRIEF DESCRIPTION OF THE DRAWINGS

The invention will be described by reference to the appended drawings, which show FIG. 1 illustrates a perspective view of an embodiment of the spine cage of the invention.

FIG. 2 illustrates a side view of an embodiment of the spine cage of the invention.

FIG. 3 illustrate a cut view along cut plane B-B of FIG. 2.

FIG. 4 illustrate a cut view along cut plane A-A of FIG. 2.

FIG. 5 illustrates a top view of an embodiment of the spine cage of the invention.

DETAILED DESCRIPTION

The figures illustrate an embodiment of the spine cage 1 of the invention.

The cage comprises an elongate body with two side faces 2-3 and a top face 4 and a bottom face 5.

Each of said faces 2-5 comprises an opening 12, 13, 14 and 15. Each of said faces also comprises a structure or pattern of regular or irregular shapes for example serrations or any other equivalent surfaces or shapes (for example teeth, pyramids etc) to maintain the cage in position. (Primary fixation)

In addition, the width of each pair of sides 2/3 and 4/5 is different, as can be understood from FIGS. 2, 3 and 5, thus forming a rectangular shape and not a square shape (see FIG. 3). This dimension is illustrated by d1 and d2 in FIGS. 2 and 5. Typically, the width d1 of sides 2/3 is larger than the width d2 of sides 4/5.

The idea here is therefore to provide a spinal cage that can be positioned at least in two different positions having two different sizes by a 90° rotation of the cage. A same cage is thus able to change its size in a very easy way, avoiding for example the complex expansion systems of the prior art.

The increment of cage width d1, d2 between each pair of sides 2/3, 4/5 might be of 0.5 mm, 1 mm or more. Alternatively, the width d1 and d2 may have a fixed proportional size or not.

As illustrated, the cage has an open structure presenting more or less the same pattern/serrated structure on every side of the cage to get a better primary fixation into the vertebral endplate.

In another embodiment (not illustrated) according to the invention the shape of a pair of sides is different from the shape of the other pair of sides.

The two pair of sides may also differ with respect to other parameters such as the structuration.

The cage according to the invention may also contain more than two pair of sides.

Hence, a same cage may be used to provide at least two different configurations depending on which position is chosen for its insertion. Since more than two faces are functional, the only choice it to find the appropriate configuration that fits the best for a given patient.

Typically, the cages according to the present invention may be provided in kits with several "configurations, for instance with variable relative sizes or proportional sides, shapes or structurations.

The present invention also concerns a method of using a spine cage as described herein. According to the method, at least one of said cage is placed in an intervertebral space.

Two cages are normally placed in said intervertebral space in case of PLIF approach. Usually only one cage in case of TLIF, XLIF and ALIF.

The examples given in the present specification are only for illustrative purposes and should not be construed in a limiting manner. Other constructions are possible using equivalent means and within the spirit and scope of the present invention. The embodiments described herein may also be combined as desired.

As mentioned previously a spine cage may comprise more than four sides, for example six or eight, wherein different sizes, shapes or angles are provided by each facing pair of sides in accordance with the principles of the present invention.

The cage of the present invention may be made in any suitable material such a metal, alloys or synthetic materials. The cage may for example be made of a material which is homogeneous or in trabecular type structure or also a combination of both.

The invention claimed is:

1. A method of inserting a spine cage between two or more vertebrae for spinal fusion, the method comprising the steps of:
providing a spine cage including a first pair of opposite functional sides having a first bone fixation structure, and a second pair of opposite functional sides having a second bone fixation structure, a cross-sectional shape of the spine cage being rectangular, both the first and second bone fixation structures configured to engage directly with the two or more vertebra for fusion;
determining whether the spine cage fits into an intervertebral space of a given patient in a first position for fusion with the two or more vertebrae or in a second position for fusion with the two or more vertebrae that is a 90° rotation of the spine cage with respect to the first position;
inserting the spine cage into the intervertebral space either in the first position or in the second position based on the determining; and
fusioning the spine cage in either the first position or in the second position based on the inserting.

2. The method of claim 1, further comprising the step of: fusioning the spine cage to the intervertebral space by transforaminal lumbar interbody fusion (TLIF), lateral lumbar interbody fusion (XLIF) and anterior Lumbar Interbody Fusion (ALIF).

3. The method of claim 1, further comprising the step of: inserting a second spine cage into the intervertebral space in posterior lumbar interbody fusion (PLIF).

* * * * *